(12) United States Patent
Reymond

(10) Patent No.: US 6,573,059 B1
(45) Date of Patent: Jun. 3, 2003

(54) USE OF THE REGULATORY SUBUNIT OF THE CAMP DEPENDENT PROTEIN KINASE (PKA) FROM DICTYOSTELIUM FOR CAMP MEASUREMENTS

(75) Inventor: Christophe D. Reymond, Prilly (CH)

(73) Assignee: RMF Dictagene S.A., Epalinges (CH)

( * ) Notice: Subject to any disclaimer, the term of this patent is extended or adjusted under 35 U.S.C. 154(b) by 0 days.

(21) Appl. No.: 09/586,605

(22) Filed: Jun. 2, 2000

(51) Int. Cl.[7] .................... C12Q 1/48; C12P 21/06; C12N 9/12; C12N 1/20; C12N 1/00
(52) U.S. Cl. .................. 435/15; 536/23.2; 536/23.4; 435/69.1; 435/194; 435/252.3; 435/320.1; 435/325; 435/69.7
(58) Field of Search .................... 536/23.2, 23.4; 435/15, 69.1, 194, 252.3, 320.1, 325

(56) References Cited

FOREIGN PATENT DOCUMENTS

| WO | WO 91/01305 | 2/1991 |
|---|---|---|
| WO | WO 92/00388 | 1/1992 |
| WO | WO 96/23898 | 8/1996 |
| WO | WO 98/40477 | 9/1998 |
| WO | WO 98/45704 | 10/1998 |
| WO | WO 98/48278 | 10/1998 |
| WO | WO 98/55873 | 12/1998 |
| WO | WO 00/49183 | 8/2000 |

OTHER PUBLICATIONS

Biondi et al., "Random insertion of GRP into the cAMP-dependent protein kinase regulatory subunit from Dictyostelium discoideum," Nucleic Acids Research., vol. 26, No. 21, Nov. 1, 1998, pp. 4946–4952.

Mucignat–Caretta et al., "Binding of two fluorescent cAMP analogues to type I and II regulatory subunits of cAMP–dependent protein kinases," Biochim Biophys Acta., vol. 1357, No. 1, Jun. 5, 1997, pp. 81–90.

Pollock et al., "Using GFP in FRET–based applications," Trends Cell Biol., vol. 9, No. 2, Feb. 1999, pp. 57–60.

Adams et al., "Fluorescence ratio imaging of cyclic AMP in single cells," Nature, vol. 349, No. 6311, Feb. 21, 1991, pp. 694–697.

Mutzel et al., GenBank accession number OKDDRC, 1987.*

Biondi et al., Nucleic Acid Research 26:4946–4952, Nov. 1, 1998.*

Romoser et al., J. Biol. Chem. 272:13270–13274, 1997.*

Mutzel et al., PIR accession No. OKDDRC, 1993.*

* cited by examiner

Primary Examiner—Rebecca E. Prouty
Assistant Examiner—Delia Ramirez
(74) Attorney, Agent, or Firm—Pillsbury Winthrop LLP

(57) ABSTRACT

The invention relates to the use of the regulatory subunit (R) of the cAMP dependent protein kinase (PKA) from *Dictyostelium discoideum* for cAMP detection. It includes constructs for expression of the R-subunit in *E. coli* and fusion to green fluorescent proteins (GFP). Fluorescence energy transfer is used as a way to monitor cAMP binding, either by using fluorescently labelled cAMP or cGMP, or by using mutant GFPs with modified absorption and emission spectra. FRET changes upon cAMP binding will allow measurement of cAMP level either in vitro or within living cells.

13 Claims, 5 Drawing Sheets

US 6,573,059 B1

USE OF THE REGULATORY SUBUNIT OF THE CAMP DEPENDENT PROTEIN KINASE (PKA) FROM DICTYOSTELIUM FOR CAMP MEASUREMENTS

FIELD OF THE INVENTION

The invention is directed to the measurement of cAMP either in vitro or within living cells. The invention further relates to molecules for use in the methods and to DNA constructs that encode the molecules.

BACKGROUND OF THE INVENTION

In molecular biology, drug testing and medical diagnostic, it is desirable to measure cAMP concentration, since intracellular cAMP is a common second messenger in many living cells. cAMP concentration in solution is currently routinely measured using either heart muscle protein extracts or antibodies (Amersham, cAMP assays, TRK432 or RPA509).

In order to measure cAMP levels, the cells need to be lysed and cAMP solubilized. Such methods require time and are prone to artifacts resulting from cAMP degradation by phosphodiesterases, incomplete lysis or masking agents. Current methods based on muscle extracts allow to measure concentrations of solubilized cAMP in the range of 0.125–32 pmol/ml and radioimmunoassay 0.25–16 pmol/ml. Acetylation allows to improve these detection limits by factors of 3 to 10. Scintillation proximity assays further simplified radioimmunoassays (Amersham, RPA538) without much improving detection thresholds.

There remains a need for better cAMP measurement methods that can be used in vitro and in vivo.

The present invention provides such methods and is based on the following observations.

The regulatory subunit of the cAMP dependent protein kinase (PKA) from Dictyostelium shows a $K_D$ for cAMP of about 20 nM, which is in the same range as mammalian enzymes 10–30 nM. It was considered that this PKA could thus represent an alternative system for the measurement of cAMP.

Furthermore, this protein can be produced within any cell by placing its gene in a proper expression vector, thus also allowing intracellular cAMP measurements.

Binding of extracellular signals, like hormones, to membrane bound receptors triggers an increase in cAMP concentration within the cell. Intracellular cAMP binds mainly to the regulatory subunit of PKA, dissociating regulatory (R) and catalytic (C) subunits. The liberated catalytic subunit is then able to phosphorylate numerous substrates, ranging from enzymes regulating metabolic pathways to transcription factors. Measurement of intracellular cAMP concentration thus reflects the activation state of a particular cell after an external stimulus. A way to trace intracellular cAMP increase has been fluorescence ratio imaging to monitor the proportion and localisation of R-C complexes (Adams et al., 1991, Nature 349, 694–697). However, the need for labelling the proteins with fluorophores in vitro and their subsequent reintroduction within calls by microinjection prevented generalisation of this method.

The cAMP dependent protein kinase (PKA) is almost ubiquitous in eukaryotic cells. In mammals PKA is composed of an haterotetramer made of two regulatory (R) and two catalytic subunits (C) which are encoded by different genes. In Dictyostelium, PKA forms only a heterodimer with one R and one C subunit. The R subunit from Dictyostelium resembles closely the mammalian RII type and can interact with mammalian C subunits (Reymond and Veron, 1995, DdPKA, cAMP-dependent PK (*D. discoideum*) In: The protein kinase Facts book, protein-serine kinases, G. Hardie and S. Hanks, eds. (London: Academic Press), pp. 70–72). However the Dictyostelium R subunit has the unique property of not forming a dimer naturally. The inventors anticipated that this should facilitate cAMP binding as well as R-C interaction studies.

There is however a need for a reporter molecule within living cells which could detect cAMP changes.

The isolation of a gene encoding a green fluorescent protein (GFP) from *Aequorea victoria* opened a new way to monitor proteins within cells non-invasively using the techniques of fluorescence microscopy or flow cytometry (Chalfie et al, 1994, Science 263, 802–805, and U.S. Pat. No. 5,491,084). The GFP protein undergoes an autocatalytic reaction involving Ser65, Tyr66 and Gly67 residues, leading to the creation of a fluorophore. A series of mutations have been introduced around amino acid 66, allowing to modify both excitation and emission wavelength (U.S. Pat. No. 5,777,079).

The use of two GFPs acting as donor and acceptor fluorophores has allowed to obtain fluorescence energy transfer (FRET). When excited at the proper wavelength, the donor GFP emits light in the range of the excitation wavelength of the acceptor GFP. FRET depends on the distance (d) between the fluorophores and decreases as a function of $d^6$, thus donor and acceptor GFPs have to be placed in close proximity. As a result of FRET, the donor emission peak is reduced, while the acceptor emission increases.

A major limitation of the use of GFPs, however, has been the insertion of the GFPs either at the N- or C-terminus of the protein of interest. This type of insertion results in many cares in an inactivation of the protein of interest.

In the research that led to the present invention it has been found that GFPs can be inserted at almost any position within the R-subunit without loosing its ability to fluoresce (Biondi et al., 1998, Nucleic Acids Research 26, 4946–52). Furthermore, functional R-subunit properties, namely cAMP binding and interaction with the C-subunit, were kept in many fusions. It was anticipated that such proteins can be used to monitor cAMP binding. However, one would prefer a test in which fluorescence changes upon cAMP binding.

According to the present invention it was now demonstrated that particular R-GFP fusions from *Dictyostelium discoideum* can be used for cAMP measurements, based on FRET changes. These R-GFP fusions can be used also within living cells. In addition, a truncated R subunit, able to bind a single cAMP molecule with high affinity, is further used to obtain simple quantification. The invention thus provides a cAMP binding protein that is modified by fusion to fluorescent proteins.

More in particular, the present invention provides DNA constructs and methods allowing to monitor by fluorescence changes the binding of cAMP to the regulatory subunit of the cAMP dependent protein kinase (PKA) from *Dictyostelium discoideum*. This method in nature is applicable both to in vitro and in vivo tests, since the gene encoding the R subunit, as well as fusions with green fluorescent proteins (GFP) can be expressed in different organisms ranging from bacteria to human cells.

In the present invention, methods and compositions are provided for producing Dictyostelium R-subunits in *E. coli*. DNA constructs allowing the expression of fusion proteins in *E. coli* are described in which donor and/or acceptor GFPs are inserted at particular locations within the R subunit allowing fluorescence energy transfer (FRET). Evidences for the occurrence of FRET are presented either between fluorescent cAMP or cGMP, or between acceptor and donor GFPs. FRET in modified upon cAMP binding Thus the GFP-R fusion proteins presented can be applied for the measurement of cAMP concentration.

Furthermore, the nature of the fused genes is compatible with expression in living cells, allowing to measure intracellular cAMP concentrations in vivo.

DETAILED DESCRIPTION OF THE INVENTION

The invention relates in particular to a DNA construct for the preparation of a fusion product, which construct comprises the coding sequence of at least one cAMP binding site of the regulatory subunit (R) of a cAMP dependent protein kinase unable to dimerise, which coding sequence is operably linked to a DNA sequence encoding a reporter polypeptide, wherein the fusion product is for use in the measurement of cAMP concentration. In a specific embodiment the cAMP dependent protein kinase is from *Dictyostelium discoideum*.

Preferably, the DNA sequence encoding the reporter protein is inserted in frame within said regulatory subunit.

However, the invention also encompasses constructs in which the DNA sequence encoding the reporter gene is in frame with one cAMP binding site of the R unit, but not in frame with the other cAMP binding site.

Figure 1:
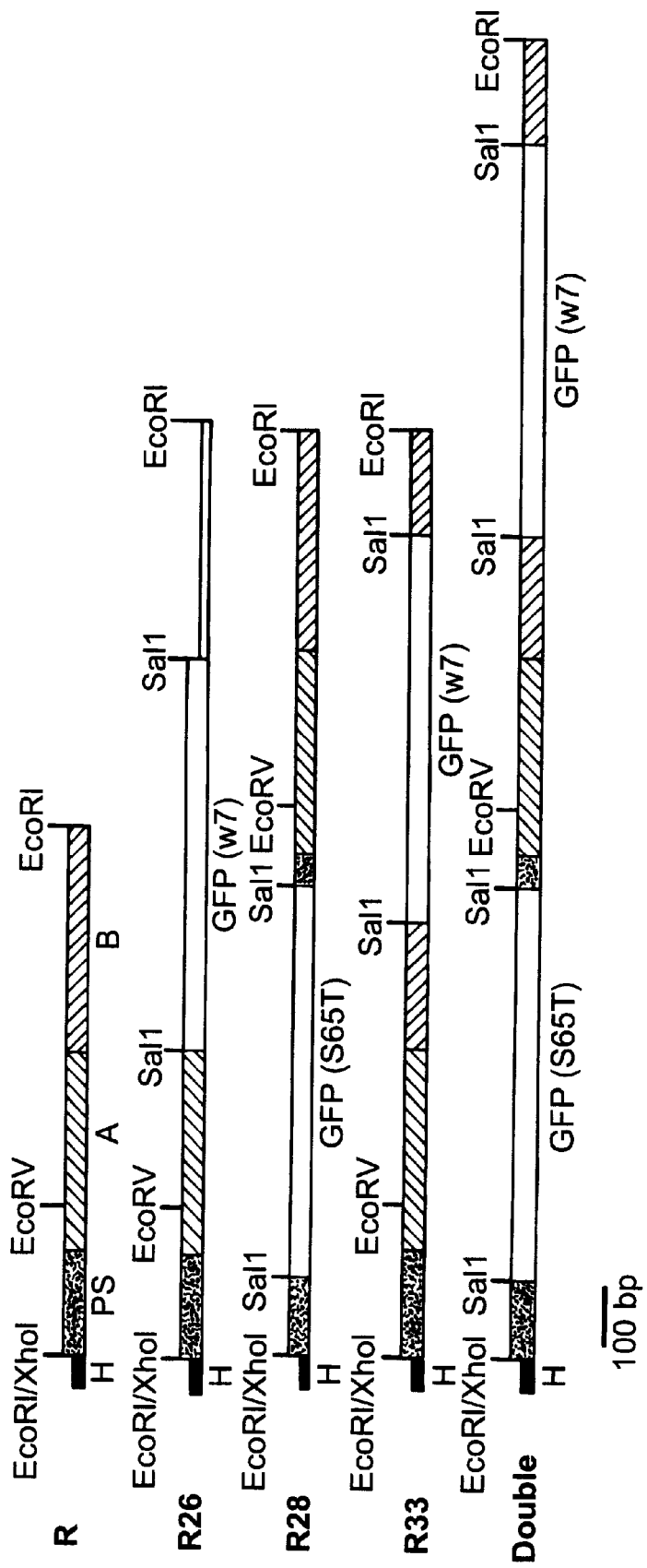
FIG. 1 is a partial map of the DNA constructs. "PS" is Promoter Sequence, "A" represents cAMP binding site A, whereas "B" is cAMP binding site B. "H" represents the His tag.

In a particular embodiment of the invention, the DNA sequence encoding the reporter protein is inserted at base 510 within the R subunit, resulting in the production of an R-protein that is truncated after amino acid 170 and fused to the reporter protein, such as for example in the construct R26 of FIG. 1.

A second embodiment of the invention relates to a DNA construct, wherein the DNA sequence encoding the reporter protein is inserted in frame after base 147 within the R subunit DNA sequence, such as for example in the construct R28 of FIG. 1.

According to a further embodiment, the DNA construct is such that the DNA sequence encoding the reporter protein is inserted in frame after base 792 within the R subunit DNA sequence, such as in the construct R33 of FIG. 1.

Furthermore, a second DNA sequence encoding a reporter protein may be inserted in frame within said R subunit DNA sequence. Preferably, both DNA sequences encoding reporter proteins are located outside one cAMP binding site on the R subunit DNA sequence. The DNA sequence encoding the first reporter protein is for example inserted at position 147 within the R subunit DNA sequence, and the DNA sequence encoding the second reporter protein is inserted at position 792 within the R subunit DNA sequence, such as in the construct Double of FIG. 1.

In the above described embodiments at least one of the DNA sequences encoding a reporter protein encodes a fluorescent protein, in particular the green fluorescent protein (GFP) from *Aequorea Victoria*. The fluorescent protein may be GFP mutant w7 or GFP mutant S65T.

Preferably, the location of the DNA sequences encoding the fluorescent proteins within the construct leads to the capability of fluorescence energy transfer (FRET) between the fluorescent proteins in the fusion product.

This is for example achieved when the location of the DNA sequences encoding the fluorescent proteins within the construct is such that in the fusion product the fluorescent proteins will be located on the same face of the regulatory subunit tertiary structure. Alternatively, the location of the DNA sequences encoding the fluorescent proteins within the construct is such that in the fusion product the fluorescent proteins are placed in such locations that FRET changes upon binding to the catalytic subunit (C).

For cAMP measurement it is preferred that the location of the DNA sequences encoding the fluorescent proteins within the construct is such that in the fusion product the fluorescent proteins are placed in such locations that FRET changes upon cAMP binding.

In a particularly advantageous embodiment, the location of the DNA sequences encoding the fluorescent proteins within the construct is such that in the fusion product the distance between the two fluorescent proteins is about 4 Å.

The invention also relates to a method for the preparation of a measuring tool for measurement of cAMP concentration, comprising a) introducing a DNA construct according to the invention in a suitable host cell;

b) expressing the fusion protein encoded by the DNA construct in the host cell; and c) isolating the fusion protein, which is the tool for measurement of cAMP concentration.

The host is a for example a bacterial host, in particular *Escherichia coli*. The purification of the fusion protein may be effected by means of Ni- and cAMP-affinity and size fractionation.

The invention also relates to the fusion protein that is encoded by the construct of the invention, which protein can be used as a tool for measuring cAMP concentration in vivo or in vitro.

The tool can be used in a method for measuring the cAMP concentration in a biological fluid, which comprises a) adding a fusion protein as claimed in claims 25 or 26 together with a defined concentration of fluorescent cyclic nucleotide to the biological fluid, b) recording fluorescence emission and determining cAMP concentration in the biological fluid by comparing the value of the fluorescence optimum with a standard curve obtained with defined concentrations of cAMP.

The fluorescent nucleotide may be selected from cGMP, (8-{{2-{(Fluoresceinylthio-ureido)amino}ethyl}thio}guanosine-3', 5'-cyclic monophosphate, cAMP and (8-{{2-{(Fluoresceinylthio-ureido)amino}ethyl}thio}adenosine-3', 5'-cyclic monophosphate.

The invention further relate to a method for inserting fluorescence donor and acceptor proteins in a cAMP dependent protein kinase regulatory subunit in order to obtain Fluorescence energy transfer (FRET), which method comprises:

a) placing a DNA construct of the invention in a suitable expression vector, b) transforming either procaryotic or eukaryotic cells with the suitable expression vector containing the DNA construct;

c) measuring FRET in living cells or extracts using the ratio of emission peaks from acceptor and donor fluorescent proteins.

In the above method the DNA construct is preferably designed such that the fluorescence donor and acceptor proteins encoded by it are placed on the same side of the regulatory subunit, or such that the fluorescence donor and acceptor proteins encoded by it are placed on both sides of a cAMP binding domain.

In the above method the FRET may be modified by binding of the catalytic subunit to the regulatory subunit or FRET is modified by binding of cAMP to the regulatory subunit.

The present invention is described with respect to the green fluorescent protein (GFP) in the following.

The *Dictyostelium discoideum* R subunit, fused to a His-tag, was expressed in *E. coli* using the pRSETb expression vector. The R subunit gene was fused to fluorescent protein encoding genes. Random insertion of either S65T or w7 mutant green fluorescent protein (GFP) gene (Biondi (1998), supra) within the Dictyostelium R-subunit resulted in the isolation of over 120 clones, some of which encoded in frame fusion proteins, others showed frameshifts past the GFP encoding region. All manipulations were as described in Biondi et al., 1998, supra.

For the present invention, particular R-GFP fusions were selected to enable measurement of the cAMP concentration, which consist of a combination of a Dictyostelium R subunit unable to dimerise, and molecules able to bind a single cAMP molecule instead of two, thus simplifying kinetics.

In a first embodiment of the invention, clone R26 was selected, which is a construct expressing a truncated R subunit fused to w7-GFP. The insertion of GFP leads to the deletion of one base pair, resulting in a frame shift past the GFP (thin line). The fusion protein of about 50 kDa contains the N-terminal part of the R subunit including a single cAMP binding site (site A, FIG. 1) fused to the w7 GFP.

R26-GFP was first purified on a Ni-NTA agarose column, based on the presence of a His-tag at its N-terminus. Proteins eluting from the column were further purified on cAMP-agarose. cGMP was used to specifically elute R26-GFP from the cAMP agarose column. Separation of cGMP, as well as possible other remaining contaminants, from R26-GFP was performed by HPLC using a BioSec SEP 3000 column.

The fluorescence of the purified R26-GFP protein showed a major emission peak at 475 nm (FIG. 2, open circles) and an excitation peak at 433 nm (data not shown), very close to the values reported for w7 (474 and 434 nm, respectively). This result confirms that fusion to the R subunit does not influence GFP fluorescence properties.

Figure 2:
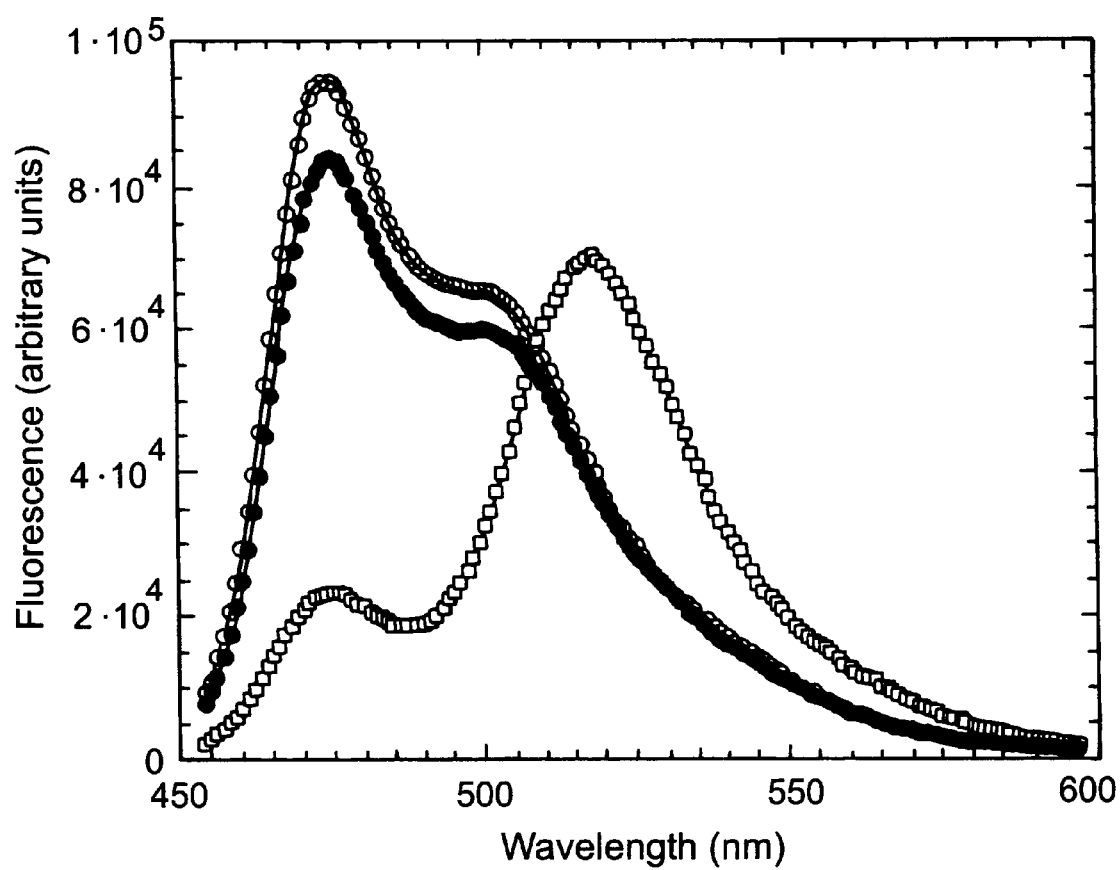
FIG. 2 shows a fluorescence spectrum of a fusion between the R subunit and GFP, R26-GFP, alone or in the presence of 8-fluo-cGMP and a cAMP competition.

Fluorescently labelled cGMP (8-{{2-{(Fluoresceinylthioureido)amino}ethyl}thio} guanosine-3', 5'-cyclic, Biolog) was added to purified R26-GFP and fluorescence emission recorded while exciting at 433 nm. Fluorescence intensity decreased at 475 nm while it increased at 520 nm, corresponding to the maximum of fluorescence for the fluorescent 8-fluo-cGMP (FIG. 2, open squares). A similar spectrum was obtained when using fluorescently labelled cAMP (8-{{2-{(Fluoresceinylthioureido)amino}ethyl}thio}adenosine-3',5'-cyclic monophosphate). Excitation at 433 nm of 8-fluo-cAMP alone gives almost undetectable emission at 520 nm, since excitation of 8-fluo-cGMP occurs around 494 nm. These results indicate that FRET occurs between the w7-GFP fused to the truncated R-subunit and 8-fluo-cGMP.

In a further experiment, unlabelled cAMP was added in a 5 fold excess over 8-fluo-cGMP. Fluorescence intensity at 475 nm increased back to a level almost identical to R26-GFP alone, while fluorescence at 520 nm decreased (FIG. 2, filled circles). Thus competition occurred between unlabelled cAMP and 8-fluo-cGMP, allowing direct measurement of unlabelled cAMP by changes in FRET.

Figure 3:
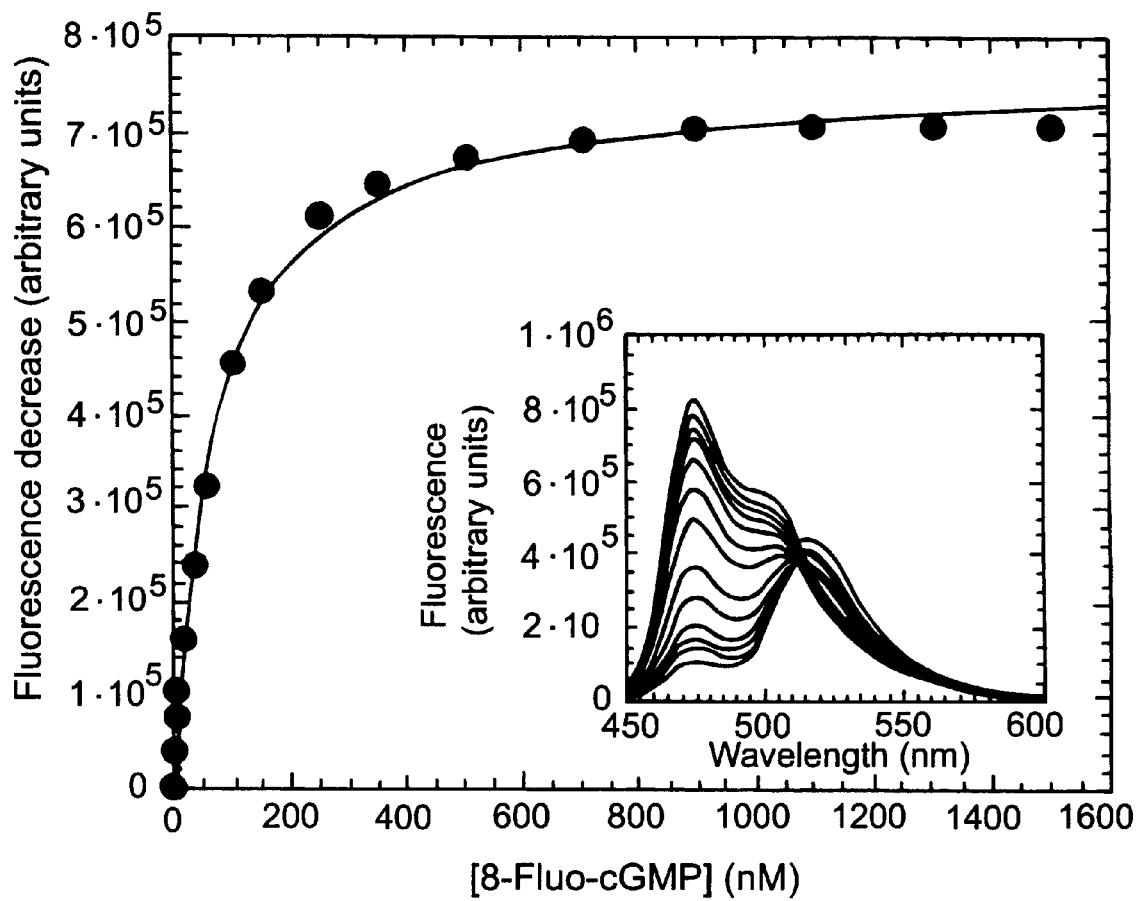
FIG. 3 shows fluorescence decrease at 475 nm plotted as a function of increasing concentration of 8-fluo-cGMP added to R26-GFP. Inset shows the original spectra.

The concentration of labelled 8-fluo-cGMP was varied while recording fluorescence changes (FIG. 3, inset). Fluorescence at 475 nm varied most and was thus used for the measurement of FRET variation. A simple quadratic relation was obtained when plotting fluorescence intensity at 475 nm versus 8-fluo-cGMP concentration, allowing to measure an apparent dissociation constant, $K_D$, of about 80±10 nM (FIG. 3).

The same experiment was performed using 8-fluo-cAMP, allowing to measure an apparent $K_D$ of about 4.5 nM.

Figure 4:
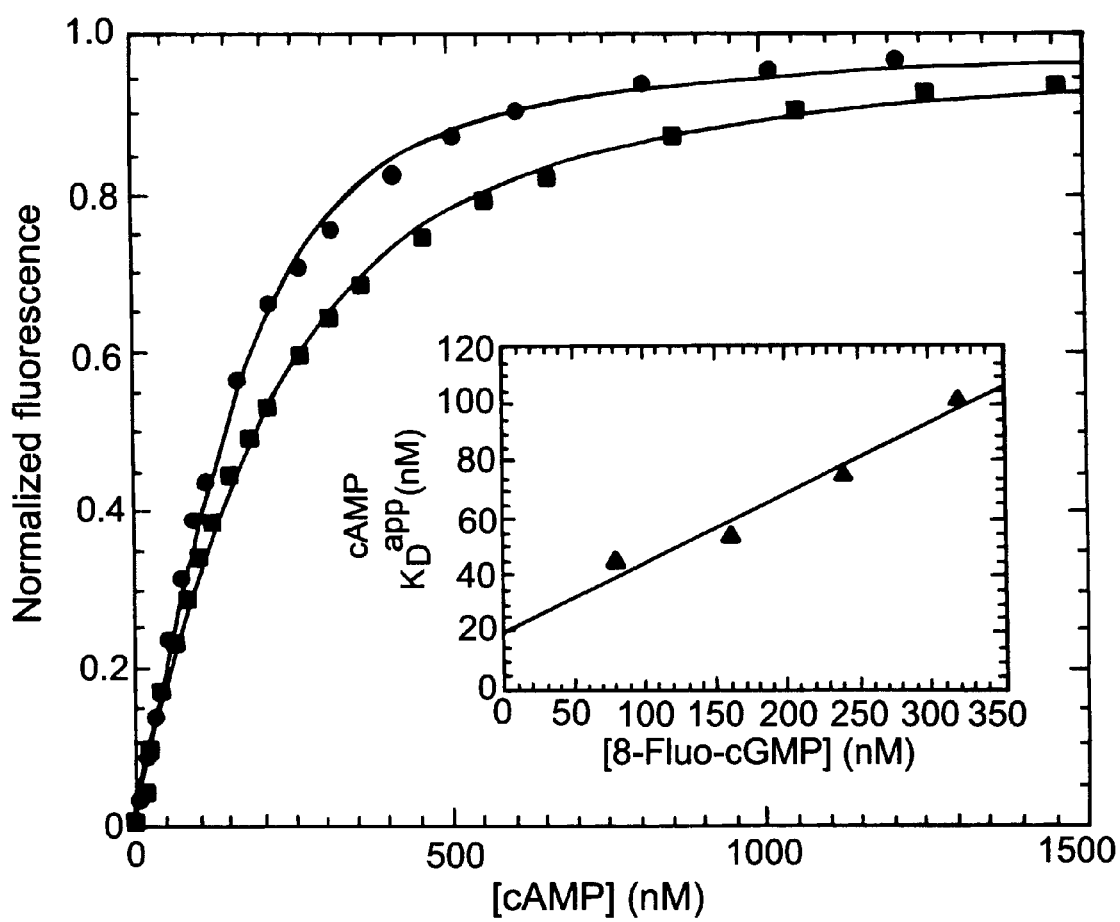
FIG. 4 shows the effect of a competition between unlabelled cAMP and 8-fluo-cGMP for binding to R26-GFP. Inset, apparent $K_D$ values plotted as a function of cAMP concentration. The true $K_D$ of 20 nM can be deduced from extrapolation to zero.

In order to measure the real $K_D$ for cAMP, a competition experiment was performed by varying stepwise 8-fluo-cGMP concentration For each 8-fluo-cGMP concentration, increasing concentrations of unlabelled cAMP was added, allowing to calculate the apparent $K_D$ for cAMP in each Case (FIG. 4). The apparent $K_D$s were in linear relation with 8-fluo-cGMP concentration, thus allowing to calculate the true $K_D$ for cAMP when extrapolating to 0 (FIG. 4, inset).

The true $K_D$ of R26-GFP for cAMP is about 20 nM±5 nM, while the reverse experiment lead to the determination of a $K_D$ of about 1.85±0.2 $\mu$M for cGMP. These experiments show that R26-GFP can be used to precisely measure cAMP in solution. This test can be applied to any sample containing cAMP, like cell lysates or biological fluids, allowing to determine its cAMP concentration by comparison with a calibration curve.

A second embodiment of the invention comprises the same principle of using the Dictyostelium R subunit and FRET changes, however in a manner compatible with in vivo measurement of cAMP concentration. Clone R28-GFP expresses the R subunit from Dictyostelium fused to the S65T GFP (FIG. 1). In clone R33 the w7-GFP is inserted within the cAMP binding site B of the R-subunit. Both fusion proteins were able to bind cAMP in solution (Biondi et al., 1998, supra). These results indicate that despite the presence of the GFP, the R subunits are properly folded, as further indicated by the ability of both R28- and R33-GFP proteins to be retained on cAMP-agarose columns.

R subunits have been well conserved throughout evolution and the Dictyostelium R can be modeled after the crystal coordinates of the mammalian enzyme. The site of insertion of the GFPs was localized on such a model. In order to obtain FRET, the donor and acceptor GFPs have to be placed in close proximity. According to the invention, fusion proteins are provided in which the insertion sites are located on the same face of the protein, in order to obtain FRET. This criterium was applied to choose the proper pair of GFP-R fusions out of the 120 random insertions. R28 and R33 fulfilled this criterium and, in addition, provided GFP insertions on either side of the cAMP binding site A of the R-subunit.

The mutant GFP w7 shows an optimum of excitation at 433 nm and of emission at 475 nm, whereas mutant S65T shows excitation and emission optima at 489 nm and 511 nm respectively (Heim and Tsien, 1996, Current Biology 6, 178–82). Both GFP mutants show important quantum yields (0.42 and 0.64 respectively). Furthermore, the emission optimum of w7 lies close to the excitation optimum of S65T, potentially allowing FRET when placed in close proximity.

Using an Xho I site flanking the R-subunit sequence and an internal Eco RV site, the R-GFP encoding fragments of R28 were combined with R33, in such a way that the fusion R-protein contains both W7 and S65T-GFPs flanking the cAMP binding site A (FIG. 1, double). The resulting gene encodes a double-GFP fusion protein with a theoretical molecular weight of 96 kDa. The constructs were made inside a pRSETb vector, under regulation of a T7 promotor, thus allowing expression of His-tagged double-GFP in *E. coli.*

Figure 5:
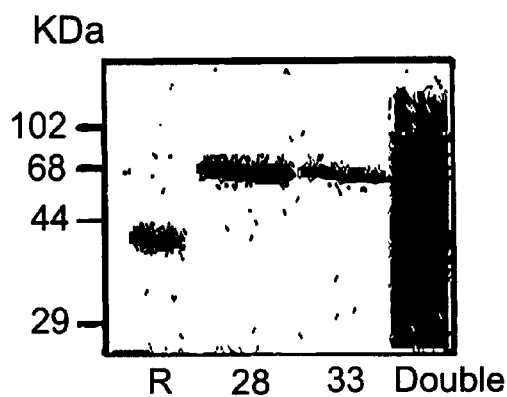
FIG. 5 shows a Western blot of the GFP-R fusion proteins R28, R33 and Double GFP expressed in *E. coli*

A Western blot of total proteins from BL21 (DE3) bacteria transformed with this construct show a protein of the expected size reacting with an anti-His-tag antibody (FIG. 5).

The double-GFP-R protein expressed in *E. coli* (BL21 DE3) was further purified. A combination of Ni-NTA-agarose and cAMP-agarose affinity chromatography and/or HPLC allowed to obtain preparations of functional double GFP-R devoid of bound nucleotides.

Figure 6A:
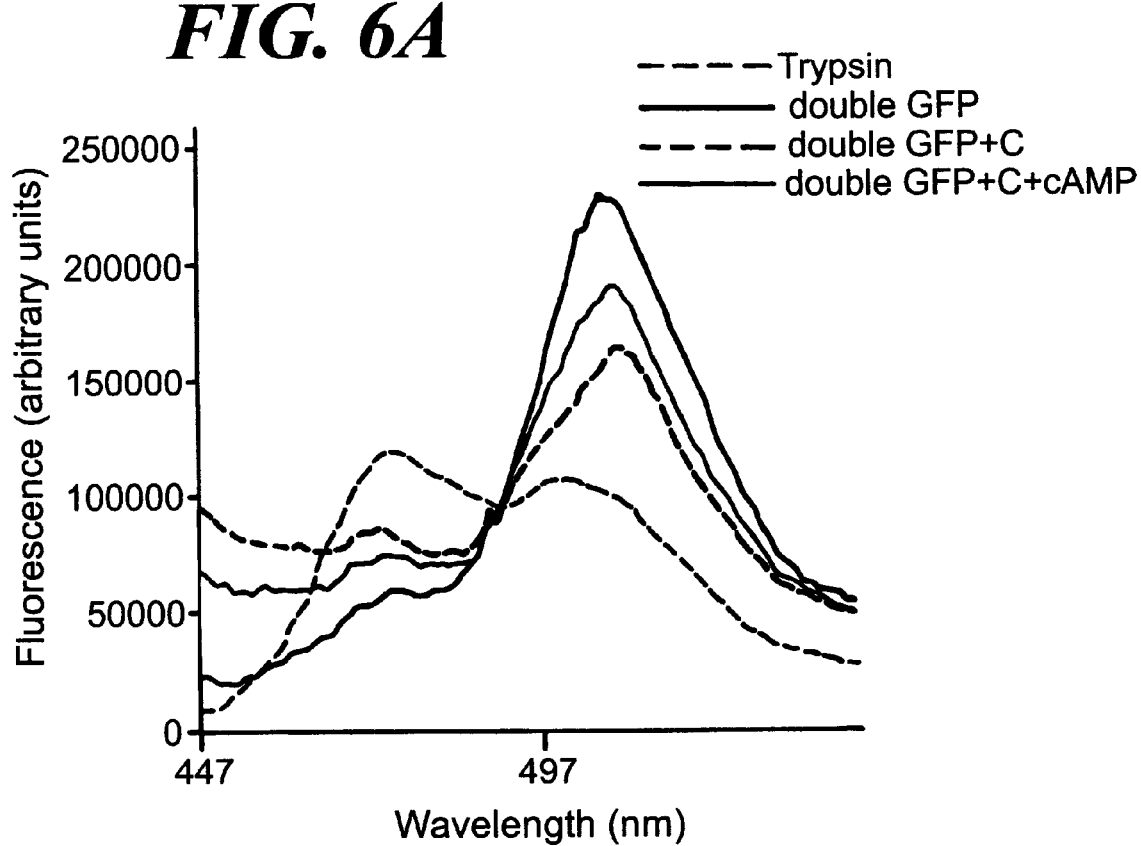
FIG. 6 shows in A, emission spectra of the double GFP-R fusion protein alone, after incubation with Trypsin, after incubation with C subunit and after incubation with C subunit and cAMP. In B, emission spectra of the same protein incubated with increasing concentration of cAMP alone.

The spectral properties of the double GFP-R were determined using a spectrofluorimeter PTI C60 with photomultiplicator. Either whole cells or partially purified proteins showed an emission profile with a shoulder between 470 and 480 nm and a clear peak at 511 nm when excited at the excitation wavelength of w7, namely 434 nm (FIG. 6A, thick black line). The shoulder corresponds to the emission of the w7, whereas the major peak represents S65T emission.

To distinguish between FRET and emission spectra of each of the GFPs, the double CFP/R was digested with Trypsin. GFPs were found to be resistant to trypsin, whereas the R subunit is attacked by trypsin. An increase in fluorescence at 475 nm and a concomitant decrease at 511 nm was observed upon proteolytic cleavage (FIG. 6A, thin gray line), which indicates that the two GFPs were diffusing apart, thus reducing FRET efficiency.

Control experiments with R28 and R33 showed basically no change in fluorescence, indicating that trypsin did not modify the fluorescence core of the GFPs themselves (data not shown). It is concluded that the combination of the two GFPs in the double GFP/R construct results in fluorescence energy transfer (FRET).

Figure 6B:
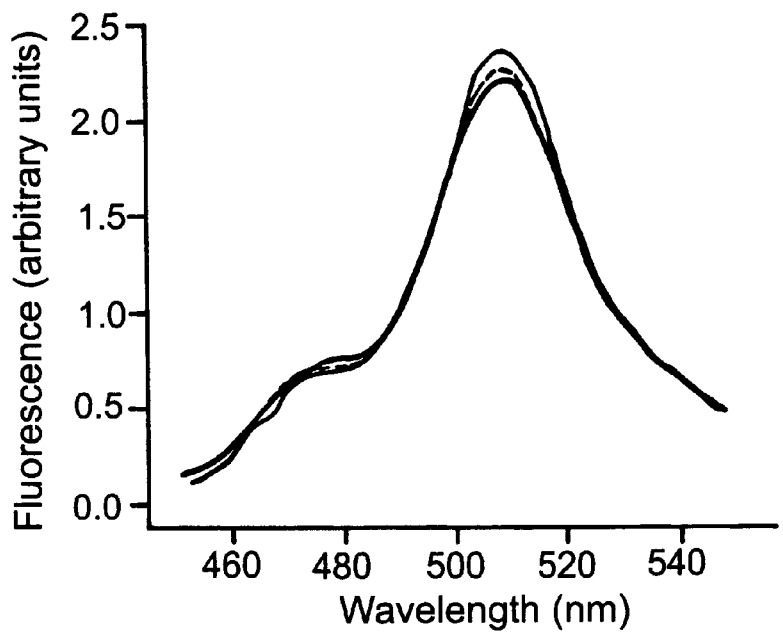

A change in conformation of the R subunit, could increase the distance between the two GFPs and thus diminish FRET. It was first analysed whether FRET changes when the R subunit binds to the C subunit. Purified C subunit from Dictyostelium was incubated in presence of double GFP/R and emission was recorded (FIG. 6A, thick gray line). The peak at 475 nm was increased, whereas the peak at 511 nm decreased, corresponding to a decrease in FRET. When the double GFP/R subunit was pre-incubated with cAMP (50 $\mu$M), the peak at 511 nm increased again, indicating that FRET was partially recovered (FIG. 6, thin black line), These results indicate that FRET is modified by binding of the double GFP/R subunit to the C subunit in a cAMP dependent manner. This allows to discriminate between free and bound R subunits based on the relative intensity of the peaks at 475 and 511 nm, setting up the path to the determination of such proportion in living cells, A conformational change could also result simply from the binding of cAMP. The double GFP-R was incubated with increasing concentrations of cAMP. As seen in FIG. 6D, only a high concentration of cAMP (500 $\mu$M, thick line) resulted in an amplitude change of only about 10% compared to double GFF/R alone (thin line), indicating that this minor FRET change can only be used to measure high concentration of cAMP.

The possibility to measure FRET on a binding protein, namely the R-subunit, opens new ways to measure cAMP concentration. It is shown according to the invention that not only FRET occurs, but that FRET is modulated by ligand binding. GFPs were fused to the complete R-protein instead of engineering fragments with terminal insertions of GFPs. FRET was obtained by placing the two mutant GFPs in close proximity on the same face of the R-subunit, as deduced from a prediction of the tertiary structure of the protein. The two sites were placed on the same face of the molecule 28

Å apart. The diameter of a GFP molecule, as deduced from its crystal structure is about 24 Å. It can thus be estimated that the distance between the sides of the two GFP barrels is of about 4 Å. An equivalent strategy can be used now on different proteins, allowing to obtain FRET. This approach is applicable to any protein for which the tertiary structure is known or can be deduced. Inserting the fluorescent proteins on the same side of the protein such that they are placed around 4 Å apart will result in fusions potentially able to transfer energy to each other.

Based on the examples described above, further protein fusions can be envisaged. A non exhaustive list of possible modifications includes truncating the R-subunit from its A site while leaving the B site intact and/or the chemical synthesis of either R- or GFP-moieties reunited by chemical ligation (allowing modification of specific amino acids). The use of mutant R-subunits with modified cAMP affinity may allow to broaden the range of cAMP concentration measurements.

Further extension of the method will include replacing the w7 and S65T GFPs fused to the R subunit by either mutant proteins with different spectral properties, or other chromophores. Other fluorescent proteins or peptides (Heim and Tsien, 1996, Koala) can be inserted instead of GFPs.

The fusion genes can be placed under different promoters and termination sequences, allowing expression in other hosts, like Dictyostelium, yeast or mammalian cells. In the latter case, the codons of both GFPs and R may be adapted for expression in mammalian cells, thus improving the level of expression of the fusion protein (Zolotukhin et al., 1996, Journal of Virology 70, 4646–4654).

The protein described here, double-GFP-R, can be used to measure cAMP concentration in vitro and in vivo. For the latter application, the double GFP-R encoding DNA is placed in expression vectors dedicated to the host chosen. Fluorescence is monitored directly in living cells. The occurrence of FRET and its modification when cAMP concentration increases within the cell is monitored by the ratio of the emission maxima of the donor and acceptor GFPs, without killing the cells. This non-invasive application is of particular interest, since modulation of cAMP level within a cell reflects its state of activation In particular, the effect of hormones on intracellular cAMP can be monitored directly in cells expressing double-GFP-R. This procedure allows to follow the effect of hormone analogs and thus can be applied to drug screenings. The advantage of such a method is that not only hormone binding is monitored, but also the ability of the designed substance to trigger biological signaling. Testing living cells thus allows to develop new drugs which agonize or antagonize receptors without affecting cell survival.

In general the use of R-subunits fused to GFP and the modifications proposed in this application give the tools necessary to measure cAMP level changes either in vitro or in vivo.

The present invention will be further illustrated in the examples that follow.

EXAMPLES

Example 1

Preparation of the vectors and expression products

A cDNA encoding the catalytic core of the R subunit from *Dictyostelium discoideum* was inserted in the expression vector pRSETb (Etchebehere et al., 1997, Eur J Biochem 248, 820–826) fused to an N-terminal His-tag (FIG. 1). The plasmid was transformed in *E. coli* BL21 (DE3) bacteria (Stratagene), allowing tho expression of a 44 kDa protein as seen by Western blots (R in FIG. 5).

Clone R26 was obtained by random insertion of GFP within the R subunit plasmid described above (Biondi et al., 1998, supra).

Purification

For large scale purification, fluorescent bacteria are scraped off a streak on LB-Agar plates with a loop and resuspended in LB broth up to an $OD_{600nm}$ of 10. 100 µl of bacterial suspension is inoculated per 10 cm Petri dish. After incubation at 22° C. for 2 to 4 days, the bacteria are scraped off the plate and resuspended in about 10 ml of LB broth for 15 Petri dishes. After centrifugation at 6000 rpm in an SS34 Sorval rotor for 10 min., the bacteria are resuspended in 10 ml of 50 mM HEPRS (pH 8.5), 150 mM NaCl and 1 tablet per 50 ml of complete protease inhibitor cocktail (Boehringer No I 6974981). 1 ml of lysozyme (10 mg/ml, Sigma) is added and the samples are incubated at room temperature for 30 min. with slight agitation.

The bacteria are lysed by three rounds of freezing in dry ice-ethanol and thawing at 22° C. $MgCl_2$ (up to 5 nM), NP40 (up to 1%), NaCl (up to 300 mM), Imidazole (up to 5 mM) and DNase I (up to 1 µg/ml) are added before incubation at room temperature for 30 min., allowing to complete lysis and fractionate bacterial DNA.

After centrifugation at 16000 rpm in an SS34 Sorval rotor for 15 min., the supernatant is mixed with 1 ml of Ni-NTA agarose (Qiagen) and incubated for 1 hr at room temperature. The slurry is loaded on a column and washed three times with 10 bed volumes of 50 mM HEPES (pH 8.5), 300 mM NaCl, 0.1% Tween 20, 5 mM Imidazole and protease inhibitors as indicated above. Elution of the His-tagged protein is obtained by raising the Imidazole concentration up to 300 mM in 50 mM HEPES (pH 8.5) and 300 mM NaCl.

For R26-GFP, a slightly modified procedure was used. R26-GFP was cultivated in liquid LB on a rotatory shaker instead of on agar plates. More precisely, a loop of frozen stock was inoculated in 30 ml of LB with Ampicillin. Incubation was carried out at 37° C. until the density reached 0.3 $OD_{600nm}$. 15 ml was diluted in 400 ml of LB and shaking was continued at 37° C. until the density reached 0.5 to 0.7 $OD_{600nm}$. IPTG was then added up to 0.5 mM and incubation continued overnight at 22° C. Centrifugation and lysis were carried out as indicated above.

The Ni-NTA eluate is then passed over a cAMP agarose column (Sigma, A-7396, about 3 µmol cAMP/ml of resin). 20 mg of resin is suspended in 10 bed volumes of 1 mM EDTA and incubated for 1 hr at room temperature. The resin is poured into a column and equilibrated by passing 10 bed volumes of washing buffer (50 mM HEPES, pH 8.5, 100 mM NaCl, 0.1% Triton X100 and 0.5 mM DTT). The sample is passed three times over the column. The column is then sequentially washed with 10 bed volumes of washing buffer containing; 1) no addition, 2) 5 mM 5'AMP (5' Adenosine monophosphate), 3) 500 mM NaCl, 4) no addition. Elution of the R-GFP is performed in 50 mM cGMP in washing buffer, at room temperature.

To eliminate cGMP from the R-GFP, the samples were passed over a Sepharose G50 column (Pharmacia) equilibrated in 50 mM Hepes pH 8.5, 100 mM NaCl, 0.1% Triton X100, 0.5 mM DTT (Dithiotreitol). R-GFP elutes in the excluded volume, whereas cGMP is retarded by the column. Alternatively the G50 column was equilibrated in a 5 fold diluted buffer and the eluted samples concentrated 5 fold by vacuum.

A further purification was sometimes achieved by passing the samples on an HPLC (Hewlett Packard 1090) with a BioSep SEC 3000 column (Phenomenex) equilibrated in 50 mM phosphate buffer pH 7.2. Fractions were collected and either assayed for inhibition of PKA catalytic activity, protein purity (Silver stained SD-PAGE electrophoresis) or Western blotting using an anti-His tag antibody.

At each step of purification, fluorescence emission spectra were recorded, exciting at 434 nm for w7 GFP. About 50% of the fluorescent material bound to the Ni-NTA agarose column, whereas only 10% was retained on the cAMP-agarose column. Final purity was less than about 50% as deduced from staining (Silver, Coomassie, or Ponceau) after SDS-PAGE.

FRET Measurements

For FRET measurements, R-26-GFP was diluted to about 0.1 µM. Excitation was performed at 433 nm, while emission was recorded over a range from 450 to 550 nm in a PTI C60 spectrofluorimeter (Photon Technology International).

Results

R26-GFP shows an peak of emission at 475 nm. Different concentrations of 8-Fluo-cGMP (8-{{2-{(Fluoresecinylthioureido)amino}ethyl}thio} guanosine 3', 5'-cyclic monophosphate, Biolog) were added as indicated (5 fold excess in FIG. 2, open squares) and emission spectra were recorded again. 8-Fluo-cGMP shows a peak of emission at 520 nm. In competition experiments, unlabelled cAMP was added at the indicated concentrations (FIG. 3, 100 µM).

Example 2

Materials

The plasmid pRSETb-R-GFP was described previously (Biondi et al, 1998, supra).

E. coli strain BL21 (DE3) was from Stratagene. Restriction enzymes and complete protease inhibitor cocktail tablets were from Boehringer Mannheim.

Fluorescence screening was performed with an inverted microscope Axiovert 25 (Zeiss) with BP 450–490 excitation filter, beamsplitter FT510 and BP 515–565 emission filter (Zeiss).

Monoclonal anti His-RGS antibodies were from Qiagen.

Western-blot detection was performed with a Chemiluminescence kit ECL from Amersham.

Prestained protein molecular weight standards for SDS-PAGE (high) were from Gibco.

Fluorescence spectra were obtained with a Photon Technology international C60 equipment, and data processed using a Felix software.

Standard techniques can be found in Sambrook et al., 1989, (Molecular Cloning. A Laboratory Manual, Cold spring Harbor Laboratory Press) when not otherwise stated.

Methods

The coordinates of the Dictyostelium catalytic core were fitted in the model of the mouse R subunit using the computer program "Swiss pdb viewer 3". Such modelling is possible due to the high conservation of the R subunit during evolution. The sites of insertion of 35 fusions with in frame GFPs were then placed. R28 and R33 were selected since not only the two insertion sites were located on the same side of the R subunit, but also the sites of insertion are placed about 28 Å apart. This combination should result in a distance of about 4 Å between the two GFP barrels, thus resulting in FRET The EcoRV-XhoI fragment from R28 (Biondi et al., 1998, supra), containing part of the R subunit fused to S65T GFP, was ligated into the pRSETb-R-w7 GFP from clone R33 from which the EcoRV-XhoI fragment, containing the R moiety, was removed. The construct was transformed into E. coli BL21 (DE3) and the presence of the double GFP-R was verified by digestion of DNA with EcoRI (2400 bp fragment).

Transformed bacteria are grown for 4 days on LB agarose at room temperature or induced overnight with IPTG as indicated above. Bacterial proteins are separated by SDS-PAGE and analysed by immunoblotting. An anti-His-RGS monoclonal antibody (diluted 1:5000) from Qiagen revealed bands of about 40 kDa and two of 70 kDa for the R-subunit, R28- and R33-GFP respectively, as expected from the fusion of the R subunit (44 kDa) with a single GFP (27 kDa). Bacteria transformed with the double GFP-R construct showed a protein of about 100 kDa, the expected size for two GFPs fused to the R-subunit (FIGS. 1 and 5). Shorter degradation products were also observed.

Double-GFP-R expressed in E. coli is purified essentially as described in Example 1. After Ni-NTA purification, multiple bands are observed on stained SDS-PAGE gels, the largest being around 100 kDa. Immunoblotting using an anti-His-RGS antibody reveals a band of about 100 kDa, the expected size for a fusion between two GFPs and the R-subunit. After cAMP agarose and G50 chromatography, the 100 kDa band represented less than 50% of the total material.

Partially purified material was analysed for fluorescence as indicated in Example 1. Emission spectra from 450 to 550 nm were recorded using a fixed excitation at 434 nm with a bandwidth of 8 nm and an integration time between 0.2 and 1 sec (FIG. 6).

Trypsin was added up to 50 µg/ml and incubation was carried out for 30 min. at room temperature before analysing fluorescence. The decrease in size of the peak at 511 nm and the concomitant increase at 475 nm indicates that FRET decreases due to Trypsin cleavage of the R subunit moiety. GFPs have been shown to be quite resistant to Trypsin cleavage.

Dictyostelium C-subunit has been expressed in E. coli (Etchebehere at al., 1997, supra). A form with a C-terminal His tag was used in a partially purified form. 5 µl of C-subunit was incubated with 100 µl of purified Double GFP-R in a final volume of 200 µl of 20 mM Tris pH 7.4, 10 mM MgCl$_2$, 1 mM ATP for 10 min. before recording emission spectrum (FIG. 6). When needed, cAMP (50 µM, final concentration) wan preincubated with double GFP-R for 5 min. at room temperature before addition of the C-subunit.

In a second experiment, partially purified double GFP-R was incubated in the presence of increasing concentration of cAMP (FIG. 6B). 1 mM cAMP already diminished significantly the emission at 511 nm (dotted line), whereas 3 mM cAMP further reduced the peak intensity (thick line). A concomitant increase around 480 nm indicated that indeed FRET was reduced by the binding of cAMP.

What is claimed is:

1. A DNA construct for the preparation of a fusion protein, wherein said construct comprises the coding sequence of at least one cAMP binding site of the regulatory subunit (R) of a cAMP-dependent protein kinase unable to dimerise from *Dictyostelium discoideum*, which coding sequence is operably linked to DNA sequences encoding at least two reporter green fluorescent proteins, wherein the fusion protein is for use in the measurement of cAMP concentration and displays fluorescence energy transfer (FRET) between said green fluorescent proteins in said fusion protein, and wherein FRET is modified upon cAMP binding.

2. The DNA construct of claim 1, wherein the DNA sequences encoding the reporter proteins are inserted in frame within said regulatory subunit (R).

3. The DNA construct of claim 1, wherein said DNA sequences encoding a reporter protein are not located within a cAMP binding site of said regulatory subunit R.

4. The DNA construct of claim 1, wherein the DNA sequence encoding one reporter protein is inserted within the R subunit DNA sequence at a point 147 base pairs downstream of the A in the AUG start codon, and the DNA sequence encoding the second reporter protein is inserted within the R subunit DNA sequence at a point 792 base pairs downstream of the A in the AUG start codon.

5. The DNA construct of claim 4, which is the construct labeled Double of FIG. 1.

6. The DNA construct of claim 1, wherein the DNA sequence encoding a green fluorescent protein encodes a green fluorescent protein (GFP) from *Aequorea victoria*.

7. The DNA construct of claim 1, wherein the fluorescent protein is a GFP mutant w7.

8. The DNA construct of claim 1, wherein the fluorescent protein is a GFP mutant S65T.

9. The DNA construct of claim 1, wherein the location of the DNA sequences encoding the fluorescent proteins within the construct is such that in the fusion protein the FRET changes upon cAMP binding to the catalytic subunit (C) of *Dictyostelium discoideum* cyclic AMP-dependent protein kinase.

10. The DNA construct of claim 2, wherein the location of the DNA sequences encoding the fluorescent proteins within the construct is such that in the fusion protein the FRET changes upon cAMP binding.

11. A method for preparing a tool for measurement of cAMP concentration, comprising
    a) introducing the DNA construct as claimed in any one of claims 1, 2, 3–5, 6–8, 9 or 10 in a suitable host cell;
    b) expressing the fusion protein encoded by the DNA construct in the host cell; and
    c) isolating the fusion protein, which is the tool for measurement of cAMP concentration.

12. The method as claimed in claim 11, wherein the host is *Escherichia coli*.

13. The method as claimed in claim 11 wherein the fusion protein is isolated by means of Ni-and cAMP-affinity and size fractionation.

* * * * *